United States Patent [19]
Peglion et al.

[11] Patent Number: 6,153,625
[45] Date of Patent: Nov. 28, 2000

[54] INDAN-1-OL COMPOUNDS

[75] Inventors: Jean-Louis Peglion, Le Vesinet; Bertrand Goument, Viroflay; Mark Millan; Adrian Newman-Tancredi, both of Le Pecq, all of France

[73] Assignee: Adir et Compagnie, Courbevoie, France

[21] Appl. No.: 09/374,161

[22] Filed: Aug. 13, 1999

[30] Foreign Application Priority Data

Aug. 21, 1998 [FR] France .................................... 98 10601

[51] Int. Cl.⁷ ...................... A61K 31/445; C07D 405/12; C07D 409/12; C07D 411/12
[52] U.S. Cl. .......................... 514/321; 514/319; 514/320; 514/324; 546/196; 546/197; 546/202; 546/205
[58] Field of Search ...................... 514/319, 320, 514/321, 324; 546/202, 205, 196, 197

[56] References Cited

U.S. PATENT DOCUMENTS 5,286,735  2/1994  Bonnaud et al. ........................ 514/321

*Primary Examiner*—Ceila Chang
*Attorney, Agent, or Firm*—The Firm of Gordon W. Hueschen

[57] ABSTRACT

A compound selected from those of formula (I):

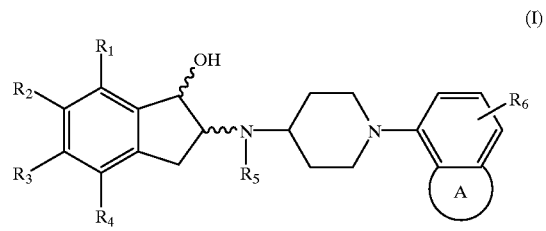

wherein:

$R_1$, $R_2$, $R_3$ and $R_4$, which may be identical or different, represent hydrogen, halogen, alkyl, alkenyl, alkynyl, hydroxy, alkoxy, trihaloalkyl, or any pair may form a heterocycle, $R_5$ represents hydrogen, alkyl, or arylalkyl, $R_6$ represents hydrogen, halogen, alkyl, hydroxy, alkoxy, or trihaloalkyl, A, together with the carbons of the phenyl, represents a heterocycle, their isomers and addition pharmaceutically-acceptable acid or base salts thereof, and medicinal products containing the same which are useful in the treatment of pathologies in which $5HT_{1B}$ receptors are involved.

19 Claims, No Drawings

INDAN-1-OL COMPOUNDS

FIELD OF THE INVENTION

The present invention relates to new indan-1-ol compounds.

DESCRIPTION OF THE PRIOR ART

Apart from the fact that they are new, the compounds of the present invention exhibit a serotoninergic activity that is especially interesting. The products of the present invention may accordingly be used as medicaments in the treatment of disorders in which involvement of the serotoninergic system has been demonstrated, such as psychiatric disorders (depression, anxiety, panic attack, schizophrenia, aggression, impulsive disorders, obsessive-compulsive disorders), degenerative diseases (Parkinson's disease, Alzheimer's disease), pain, migraine, headaches, cerebral vascular accidents, bulimia, anorexia, drug abuse and also in cardiovascular disorders (unstable angina) since, like the central nervous system, the serotoninergic system is also present in the cardiovascular areas. Numerous serotonin receptors have been identified and recently have been cloned. They have been classified into seven major classes $5HT_1$ to $5HT_7$, on the basis of their primary structure and their mode of coupling with the transduction systems (Molecular Biology of 5HT Receptors, *Neuropharmacol.,* 1994, 33, 275). Those classes are themselves sub-divided into sub-types. Sub-types $5HT_{1A}$, $5HT_{1B}$ (formerly $5HT_{1D\beta}$) and $5HT_{1D}$ (formerly $5HT_{1D\alpha}$) are known for the $5HT_1$ receptor (for a recent review and discussion of the nomenclature see *Trends in Pharmacol. Sciences,* 1996, 17, 103).

The application of the present invention concerns more especially the $5HT_{1B}$ receptor since the products of the invention act as powerful and selective ligands of that receptor. $5HT_{1B}$ receptors are located post-synaptically in the cerebral region and on the peripheral sympathetic nerve-endings, the cerebral blood vessels and the trigeminal primary afferent nerves (*Naunyn-Schmiedeberg's Arch. Pharmacol.,* 1990, 342, 371; *Mol. Pharmacol.,* 1993, 44, 242; *Eur. J. Pharmacolo.,* 1992, 227, 357). Their location implies that, by activation of $5HT_{1B}$ receptor populations, it is possible to treat migraines and headaches with agonists by both a vascular and neurogenic effect. With antagonists it should be possible by action on the peripheral receptors to treat disorders of the cardiovascular system, such as unstable angina. In addition, the populations of $5HT_{1B}$ receptors, which are also present in high concentrations in the cornu dorsale of the spinal cord, the basal ganglia, the hippocampus and the other limbic structures of the frontal cortex (*Naunyn-Schmiedeberg's Arch. Pharmacol.,* 1992, 347, 248; *Eur. J. Pharmacol,* 1992, 222, 137; *J. Neurochem.,* 1995, 65, 2671), may be partly responsible for disorders of mood and behaviour and may be involved in the mechanisms of nociception. On the basis of their dual location, on the one hand on the post-synaptic serotoninergic neurons and on the other hand on cell bodies where they assume the role of autoreceptors, their involvement in pathogenesis can easily be deduced, and consequently selective ligands of those receptors may be used in the treatment of depression, anxiety, impulsive disorders and other psychiatric disorders associated with dysfunction of serotoninergic transmission (*Neurochem. Res.,* 1990, 15, 567 *J. Neurochem.,* 1988, 51, 1906).

With respect to the $5HT_{1B}$ (formerly $5HT_{1D\beta}$) receptor, that receptor is predominant in the central nervous system of humans and guinea pigs. Furthermore, only $5HT_{1B}$ receptors are present as autoreceptors, which is not true of $5HT_{1D}$ (formerly $5HT_{1D\alpha}$) receptors. $5HT_{1B}/5HT_{1D}$ receptor ligands have been described in the Applications WO 96/00720 and WO 96/12713: they are naphthylpiperazine compounds. $5HT_{1B}/5HT_{1D}$ receptor antagonists having a biphenyl structure have been described in the Application WO 96/19477. Those structures in no way suggest the compounds of the present invention. The Patent Application WO 95/07274 describes compounds used in the treatment of disorders of the central nervous system having a 4-aminopiperidine structure. In the general formula of the said compounds the extracyclic nitrogen is bonded by way of an alkane chain to benzodioxane, tetrahydronaphthalene and chroman nuclei. Those structures do not result in the structures of the present invention.

DETAIL DESCRIPTION OF THE INVENTION

More specifically, the present invention relates to the compounds of formula (I):

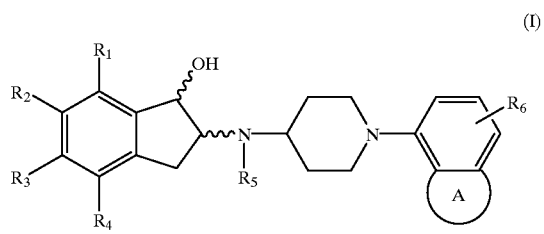

wherein:
$R_1$, $R_2$, $R_3$ and $R_4$, which may be identical or different, each represents independently of the others a hydrogen atom, a halogen atom, a linear or branched $(C_1-C_6)$alkyl group, a linear or branched $(C_2-C_6)$alkenyl group, a linear or branched $(C_2-C_6)$alkynyl group, a hydroxy group, a linear or branched $(C_1-C_6)$alkoxy group or a linear or branched $(C_1-C_6)$trihaloalkyl group, or any one or more pairs in adjacent positions may form, together with the carbon atoms of the phenyl nucleus to which they are bonded, a heterocycle, $R_5$ represents a hydrogen atom, a linear or branched $(C_1-C_6)$ alkyl group or an aryl-$(C_1-C_6)$alkyl group in which the alkyl moiety may be linear or branched, $R_6$ represents a hydrogen atom, a halogen atom, a linear or branched $(C_1-C_6)$alkyl group, a hydroxy group, a linear or branched $(C_1-C_6)$alkoxy group or a linear or branched $(C_1-C_6)$trihaloalkyl group, A, together with the carbon atoms of the phenyl nucleus to which it is bonded, represents a heterocycle, to isomers thereof and addition salts thereof with a pharmaceutically acceptable acid or base.

A heterocycle is understood as being a monocyclic, 5- to 7-membered group optionally containing one or two unsaturations additional to that due to the linkage of the said heterocycle to the phenyl nucleus with which it is fused and containing one, two or three identical or different hetero atoms selected from oxygen, sulphur and nitrogen. An aryl group is understood as being a phenyl, naphthyl, dihydronaphthyl or tetrahydronaphthyl group.

According to an advantageous variant of the invention, preferred compounds are those wherein A, together with the carbon atoms of the phenyl nucleus to which it is bonded, represents a 6-membered heterocycle containing at least one oxygen atom. A, together with the phenyl nucleus to which it is bonded, preferably represents a chroman or 2,3-dihydro-1,4-benzodioxin group.

The substituent $R_5$ preferred in accordance with the invention is a hydrogen atom.

Advantageously, preferred compounds of the invention are those wherein $R_1$, $R_2$, $R_3$ and $R_4$, which may be identical or different, each represents independently of the others a hydrogen atom, a halogen atom or a linear or branched ($C_1$–$C_6$)alkyl group, or any one or more pairs in adjacent positions may form, together with the carbon atoms of the phenyl nucleus to which they are bonded, a 5-membered heterocycle containing one or two oxygen atoms.

The substituent $R_6$ preferred in accordance with the invention is a hydrogen atom or a halogen atom.

Especially advantageously, preferred compounds of the invention are:

- 2-{[1-(3,4-dihydro-2H-chromen-8-yl)-4-piperidyl]amino}-5-fluoro-1-indanol,
- 2-{[1-(2,3-dihydro-1,4-benzodioxin-5-yl)-4-piperidyl]amino}-1-indanol,
- 2-{[1-(3,4-dihydro-2H-chromen-8-yl)-4-piperidyl]amino}-6-fluoro-1-indanol,
- 2-{[1-(2,3-dihydro-1,4-benzodioxin-5-yl)-4-piperidyl]amino}-6-methyl-1-indanol,
- 2-{[1-(3,4-dihydro-2H-chromen-8-yl)4-piperidyl]amino}-5,6-methylenedioxy-1-indanol,
- and 2-{[1-(3,4-dihydro-2H-chromen-8-yl)-4-piperidyl]amino}-5,6-dihydrofuro[2,3-b]indan-1-ol.

The isomers, and also addition salts with a pharmaceutically acceptable acid or base, of the preferred compounds are an integral part of the invention.

Among the pharmaceutically acceptable acids there may be mentioned, without implying any limitation, hydrochloric, hydrobromic, sulphuric, phosphonic, acetic, trifluoroacetic, lactic, pyruvic, malonic, succinic, glutaric, fumaric, tartaric, maleic, citric, ascorbic, methanesulphonic, camphoric acid etc.

Among the pharmaceutically acceptable bases there may be mentioned, without implying any limitation, sodium hydroxide, potassium hydroxide, triethylamine, tert-butylamine etc . . . .

The invention relates also to a process for the preparation of the compounds of formula (I), which process is characterised in that there is used as starting material a compound of formula (II):

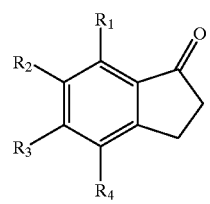

(II)

wherein $R_1$, $R_2$, $R_3$ and $R_4$ are as defined for formula (I), which compounds of formula (II) are reacted with isoamyl nitrite, in the presence of hydrochloric acid in methanol, to yield the compounds of formula (III):

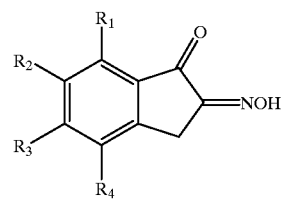

(III)

wherein $R_1$, $R_2$, $R_3$ and $R_4$ are as defined hereinbefore, which compounds of formula (III) are placed in the presence of a reducing agent to yield the compounds of formula (IV):

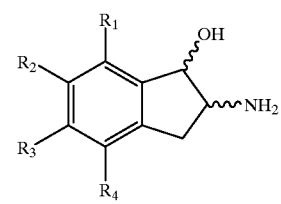

(IV)

wherein $R_1$, $R_2$, $R_3$ and $R_4$ are as defined hereinbefore, which compounds of formula (IV) are treated, under conditions of reductive amination, with a compound of formula (V):

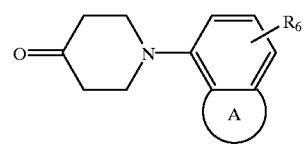

(V)

wherein A and $R_6$ are as defined for formula (I), to yield the compounds of formula (I/a), a particular case of the compounds of formula (I):

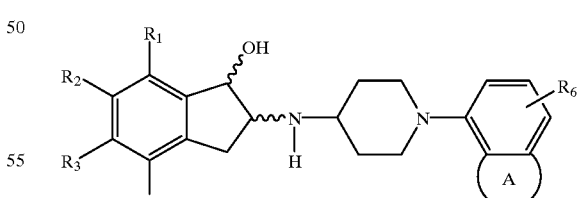

(I/a)

wherein $R_1$, $R_2$, $R_3$, $R_4$, $R_6$ and A are as defined hereinbefore, which compounds of formula (I/a) are separated according to conventional separation techniques (distillation, recrystallisation, chromatography) into the following two compounds of formulae (I/a cis) and (I/a trans), particular cases of the compounds of formula (I):

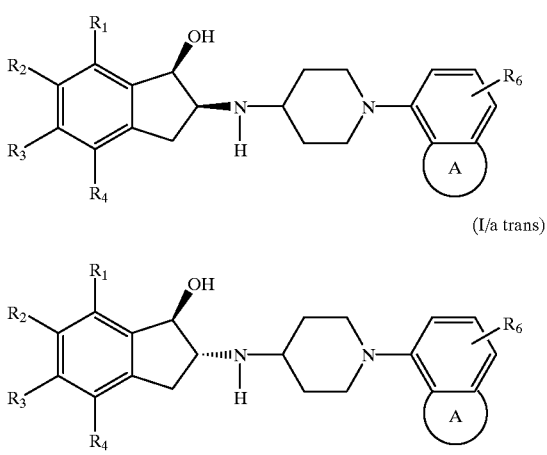

(I/a cis)

(I/a trans)

wherein $R_1$, $R_2$, $R_3$, $R_4$, $R_6$ and A are as defined hereinbefore, the secondary amine function of which compounds of formulae (I/a), (I/a cis) and (I/a trans) is substituted, if desired, according to conventional techniques of organic chemistry using a compound of formula (VI):

$$R'_5\text{---}Z \qquad (VI),$$

wherein $R'_5$ represents a linear or branched $(C_1-C_6)$alkyl group or an aryl-$(C_1-C_6)$alkyl group in which the alkyl moiety may be linear or branched, and Z represents a leaving group, to yield the compounds of formulae (I/b), (I/b cis) and (I/b trans), respectively:

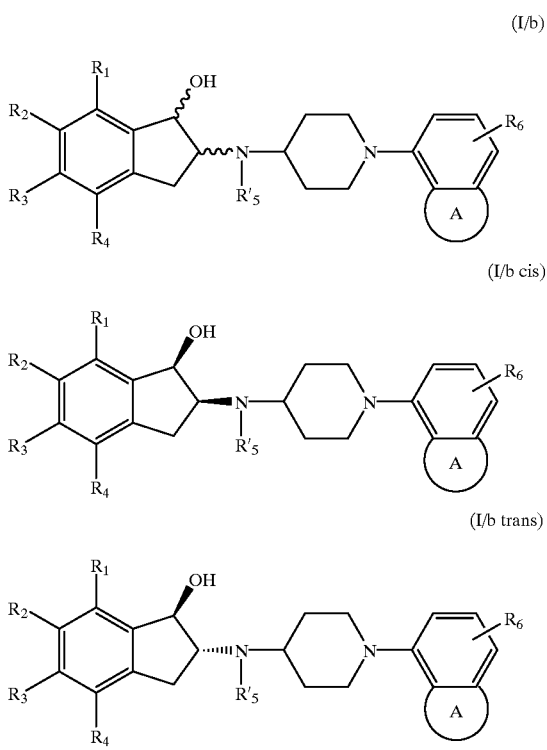

(I/b)

(I/b cis)

(I/b trans)

wherein $R_1$, $R_2$, $R_3$, $R_4$, $R_5$, $R_6$ and A are as defined hereinbefore, which compounds of formulae (I/a), (I/b), (I/a cis), (I/a trans), (I/b cis) and (I/b trans), which constitute the totality of the compounds of formula (I), are, if necessary, purified according to a conventional purification technique, are optionally separated into their isomers according to a conventional separation technique and, if desired, are converted into their addition salts with a pharmaceutically acceptable acid or base.

The compounds of formulae (II), (V) and (VI) are either commercially available or are obtained according to conventional methods of organic synthesis.

The compounds of formula (I) exhibit excellent selective affinity for $5HT_{1B}$ serotoninergic receptors. It has been possible to assess that selectivity for $5HT_{1B}$ receptors in binding experiments, especially compared with $5HT_{1A}$ receptors. The compounds of the present invention are therefore valuable in the treatment of disorders in which $5HT_{1B}$ receptors are involved.

The present invention relates also to pharmaceutical compositions comprising as active ingredient at least one compound of formula (I), an isomer thereof or an addition salt thereof with a pharmaceutically acceptable base or acid, alone or in combination with one or more pharmaceutically acceptable, inert, non-toxic excipients or carriers.

Among the pharmaceutical compositions according to the invention there may be mentioned more especially those that are suitable for oral, parenteral (intravenous, intramuscular or subcutaneous), per- or trans-cutaneous, nasal, rectal, perlingual, ocular or respiratory administration and especially tablets or dragées, sublingual tablets, sachets, soft gelatin capsules, hard gelatin capsules, lozenges, suppositories, creams, ointments, dermal gels, injectable or drinkable preparations, aerosols, eye or nose drops etc.

The dosage used varies according to the age and weight of the patient, the route of administration, the nature and severity of the disorder and the administration of any associated treatments, and ranges from 0.5 to 25 mg of active ingredient in one or more administrations per day.

The Examples which follow illustrate the invention but do not limit it in any way.

The starting materials used are materials that are known or that are prepared according to known procedures.

The various Preparations yield synthesis intermediates that are useful in the preparation of the compounds of the invention.

The structures of the compounds described in the Examples and in the Preparations have been determined according to customary spectrophotometric techniques (infrared, nuclear magnetic resonance, mass spectrometry . . . ). The melting points have been determined using either a Kofler hot-plate (K.) or a hot-plate under a microscope (M.K.).

Preparation 1:1-(Chroman-8-yl)piperidin-4-one

Step 1: 8-Nitro-2H-chromene

A solution of 20 g of 8-nitro-4-chromanone and 3.9 g of sodium borohydride in 200 ml of ethanol is heated at reflux for 45 minutes and then evaporated to dryness. The residue is taken up in 200 ml of water and extracted three times with 250 ml of dichloromethane each time. The combined organic phases are dried over magnesium sulphate, filtered and then concentrated under reduced pressure. The liquid residue is taken up in 300 ml of toluene; 0.5 g of para-toluenesulphonic acid is then added and heating at reflux is carried out until the full amount of water expected has been recovered. After cooling, washing with a 5% sodium carbonate solution and then with water, and concentrating under reduced pressure, a liquid residue corresponding to the expected product is isolated.

Step 2: 8-Amino-chroman

The product obtained in the previous Step is hydrogenated in the presence of platinum oxide in methanol to yield, after evaporation and acid-base passage, the expected product.

Step 3: 1-(Chroman-8-yl)piperidin-4-ol

A solution of 6.3 g of the product obtained in the previous Step, 6.6 g of 1,5-dichloro-pentan-3-ol, 11.65 g of potassium carbonate and 3.16 g of sodium iodide in 23 ml of dimethylformamide is heated for 1.5 hours. After returning to ambient temperature, 230 ml of water are added and the solution is then extracted with ether. After drying the organic phase over magnesium sulphate, filtering and concentrating under reduced pressure, an oil corresponding to the expected product is obtained.

Step 4: 1-(Chroman-8-yl)piperidin-4-one 3.6 ml of trifluoroacetic acid are added dropwise to a solution of 8.5 g, cooled to 5° C., of the product obtained in the previous Step, 29.9 g of dicyclohexylcarbodiimide, 5.4 ml of pyridine and 115 ml of dimethyl sulphoxide in 207 ml of toluene. After reaction for 24 hours at ambient temperature, 400 ml of ethyl acetate are added and the solution is then filtered. The filtrate is subsequently washed with water and then with a saturated sodium chloride solution, dried over magnesium sulphate and then concentrated under reduced pressure. Chromatography on silica gel (dichloromethane/ethyl acetate: 95/5) allows the expected product to be isolated.

Preparation 2: 1-(2,3-Dihydro[1,4]benzodioxin-5-yl) piperidin-4-one

The procedure is as in Preparation 1, starting at Step 3 and using 5-amino-2,3-dihydro[1,4]benzodioxin as substrate in Step 3.

Preparation 3: 1-7-Chloro-2,3-dihydro[1,4]benzodioxin-5-yl)piperidin-4-one

The procedure is as in Preparation 1, starting at Step 3 and using 5-amino-7-chloro-2,3-dihydro[1,4]benzodioxin as substrate in Step 3.

EXAMPLE 1

(cis)-2-{[1-(3,4-Dihydro-2H-chromen-8-yl)-4-piperidyl] amino}-5-fluoro-1-indanol Step A: 5-Fluoro-2-hydroxyimino-1-indanone 15 ml of isoamyl nitrite and then 7.5 ml of concentrated hydrochloric acid are added dropwise to a solution, heated to 40° C., of 11.2 g of 5-fluoro-1-indanone in 185 ml of methanol. After reaction for 45 minutes at 40° C., the reaction mixture is cooled with ice. A precipitate is formed, which is filtered off and then dried in vacuo, allowing the expected product to be isolated.

Step B: 2-Amino-5-fluoro-1-indanol (cis/trans mixture)

The product obtained in Step A dissolved in 70 ml of tetrahydrofuran is added dropwise, in the course of 30 minutes, to a suspension of 2.67 g of lithium aluminium hydride in 15 ml of tetrahydrofuran. After stirring for 30 minutes at ambient temperature and then after 12 hours at reflux of the solvent, the reaction mixture is cooled and then carefully hydrolysed using, in succession, 1.9 ml of water, 1.5 ml of 20% sodium hydroxide solution and then 6.7 ml of water. The solution is subsequently stirred for 3 hours at ambient temperature and then filtered, rinsed with tetrahydrofuran and evaporated to dryness. Chromatography on silica gel (dichloromethane/methanol/ammonium hydroxide: 95/5/0.5) allows the expected product to be isolated in the proportion of 54% of the cis product and 46% of the trans product.

Step C: (cis)-2-{[1-(3,4-Dihydro-2H-chromen-8-yl)-4-piperidyl]amino}-5-fluoro-1-indanol 1.63 g of sodium triacetoxyborohydride and 0.31 ml of acetic acid are added rapidly to 0.92 g of the mixture obtained in Step B and 1.27 g of the product obtained in Preparation 1 dissolved in 40 ml of 1,2-dichloroethane. After reaction for 48 hours at ambient temperature, the reaction mixture is poured into 40 ml of 1N sodium hydroxide solution and then extracted with 80 ml of ether. After filtering off the insoluble material, the aqueous phase is again extracted with ether. The combined organic phases are dried over magnesium sulphate, filtered and then concentrated under reduced pressure. Chromatography on silica gel (dichloromethane/methanol: 96/4) followed by recrystallisation from acetonitrile allows the expected product to be isolated.

Melting point: 172–174° C. (M.K.)
Elemental microanalysis:

|            | % C   | % H  | % N  |
|------------|-------|------|------|
| calculated | 72.23 | 7.11 | 7.32 |
| found      | 72.51 | 7.24 | 7.32 |

EXAMPLE 2

(trans)-2-{[1-(3,4-Dihydro-2H-chromen-8-yl)-4-piperidyl] amino}-5-fluoro-1-indanol The insoluble material obtained in Step C of Example 1 is recrystallised twice from acetonitrile, allowing the expected product to be isolated.

Melting point: 176–178° C. (M.K.)
Elemental microanalysis:

|            | % C   | % H  | % N  |
|------------|-------|------|------|
| calculated | 72.23 | 7.11 | 7.32 |
| found      | 72.34 | 7.23 | 7.36 |

EXAMPLE 3

(cis)-2-{[1-(2,3-Dihydro-1,4-benzodioxin-5-yl)-4-piperidyl]-amino}-1-indanol

The procedure is as in Example 1, Steps A to C, using 1-indanone as substrate in Step A and, in Step C, using the product obtained in Preparation 2 instead of the product obtained in Preparation 1.

Melting point: 178–180° C. (M.K.)
Elemental microanalysis:

|            | % C   | % H  | % N  |
|------------|-------|------|------|
| calculated | 72.11 | 7.15 | 7.64 |
| found      | 72.00 | 7.03 | 7.63 |

EXAMPLE 4

(trans)-2-{[1-(2,3-Dihydro-1,4-benzodioxin-5-yl)-4-piperidyl]-amino}-1-indanol

The procedure is as in Example 2, starting from the insoluble material obtained in Step C of Example 3.

Melting point: 199–201° C. (M.K.)
Elemental microanalysis:

|  | % C | % H | % N |
|---|---|---|---|
| calculated | 72.11 | 7.15 | 7.64 |
| found | 71.79 | 7.59 | 7.49 |

EXAMPLE 5
(cis)-2-{[1-(7-Chloro-2,3-dihydro-1,4-benzodioxin-5-yl)-4-piperidyl]amino}-6-fluoro-1-indanol The procedure is as in Example 1, Steps A to C, using 6-fluoro-1-indanone as substrate in Step A and, in Step C, using the product obtained in Preparation 3 instead of the product obtained in Preparation 1.
  Step A: 6-Fluoro-2-hydroxyimino-1-indanone
  Step B: 2-Amino-6-fluoro-1-indanol (cis/trans mixture)
  Step C: (cis)-2-{[1-(7-Chloro-2,3-dihydro-1,4-benzodioxin-5-yl)-4-piperidyl]amino}-6-fluoro-1-indanol
  Melting point 184–186° C. (M.K.)

EXAMPLE 6
(trans)-2-{[1-(7-Chloro-2,3-dihydro-1,4-benzodioxin-5-yl)-4-piperidyl]amino}-6-fluoro-1-indanol The procedure is as in Example 2, starting from the insoluble material obtained in Step C of Example 5.
  Melting point: 193–197° C. (M.K.)

EXAMPLE 7
(cis)-2-{[1-3,4-Dihydro-2H-chromen-8-yl)-4-piperidyl]amino}6-fluoro-1-indanol The procedure is as in Example 1, Steps A to C, using as substrate in Step A the compound obtained in Step A of Example 5 and as substrate in Step C, the compound obtained in Step B of Example 5.
  Melting point: 179–181° C. (M.K.)

EXAMPLE 8
(trans)-2-{[1-(3,4-Dihydro-2H-chromen-8-yl)-4-piperidyl]amino}-6-fluoro-1-indanol The procedure is as in Example 2, starting from the insoluble material obtained in Step C of Example 7.
  Melting point: 199–204° C. (M.K.)

EXAMPLE 9
(cis)-2-{[1-(3,4-Didydro-2H-chromen-8-yl)-4-piperidyl]amino}5,6-methylenedioxy-1-indanol The procedure is as in Example 1, Steps A to C, using 5,6-methylenedioxy-1-indanone as substrate in Step A.
  Step A: 2-Hydroxyimino-5,6-methylenedioxy-1-indanone
  Step B: 2-Amino-5,6-methylenedioxy-1-indanol (cis/trans mixture)
  Step C: (cis)-2-{[1-(3,4-Dihydro-2H-chromen-8-yl)-4-piperidyl]amino}-5,6-methylenedioxy-1-indanol
  Melting point: 180–183° C. (M.K.)

EXAMPLE 10
(trans)-2-{[1-(3,4-Dihydro-2H-chromen-8-yl)-4-piperidyl]amino}-5,6-methylenedixoy-11-indanol The procedure is as in Example 2, starting from the insoluble material obtained in Step C of Example 9.
  Melting point: 179–181° C. (M.K.)

EXAMPLE 11
(cis)-2-{[1-(3,4-Dihydro-2H-chromen-8-yl)-4-piperidyl]amino}-5,6-dihydrofuro[2,3-b]indan-1-ol The procedure is as in Example 1, Steps A to C, using 5,6-dihydrofuro[2,3-b]indan-1-one as substrate in Step A.
  Step A: 2-Hydroxyimino-5,6-dihydrofuro[2,3-b]indan-1-one
  Step B: 2-Amino-5,6-dihydrofuro[2,3-b]indan-1-ol (cis/trans mixture)
  Step C: (cis)-2-{[1-(3,4-Dihydro-2H-chromen-8-yl)-4-piperidyl]amino}-5,6-dihydrofuro[2,3-b]indan-1-ol
  Melting point: 201–203° C. (M.K.)

EXAMPLE 12
(trans)-2-{[1-(3,4-Dihydro-2H-chromen-8-yl)-4-piperidyl]amino}-5,6-dihydrofuro[2,3-b]indan-1-ol The procedure is as in Example 2, starting from the insoluble material obtained in Step C of Example 11.
  Melting point: 193–195° C. (M.K.)

EXAMPLE 13
(cis)-2{[1-(3,4-Dihydro-2H-chromen-8-yl)-4-piperidyllamino]-6, 7-dimethyl-1-indanol The procedure is as in Example 1, Steps A to C, using 6,7-dimethyl-1-indanone as substrate in Step A.
  Step A: 6,7-Dimethyl-2-hydroxyimino-1-indanone
  Step B: 2-Amino-6,7-dimethyl-1-indanol (cis/trans mixture)
  Step C: (cis)-2-{[1-(3,4-Dihydro-2H-chromen-8-yl)-4-piperidyl]amino}-6,7-dimethyl-1-indanol
  Melting point: 158–160° C. (M.K.)

EXAMPLE 14
(cis)-2-{[1-(3,4-Dihydro-2H-chromen-8-yl)-4-piperidyl]amino}-4,7-dimethyl-1-indanol The procedure is as in Example 1, Steps A to C, using 4,7-dimethyl-1-indanone as substrate in Step A.
  Step A: 4,7-Dimethyl-2-hydroxyimino-1-indanone
  Step B: 2-Amino-4,7-dimethyl-1-indanol (cis/trans mixture)
  Step C: (cis)-2-{[1-(3,4-Dihydro-2H-chromen-8-yl)-4-piperidyl]amino}-4,7-dimethyl-1-indanol
  Melting Point: 169–172° C. (M.K.)

EXAMPLE 15
(trans)-2-{[1-(3,4-Dihydro-2H-chromen-8-yl)-4-piperidyl]amino}-4,7-dimethyl-1-indanol The procedure is as in Example 2, starting from the insoluble material obtained in Step C of Example 14.
  Melting point: 154–156° C. (M.K.)

EXAMPLE 16
(cis)-2-{[1-(2,3Dihydro-1,4-bezodioxin-5-yl_-4-piperidyl]amino}-6-methyl-1-indanol The procedure is as in Example 1, Steps A to C, using 6-methyl-1-indanone as substrate in Step A and, in Step C, using the product obtained in Preparation 2 instead of the product obtained in Preparation 1.
  Step A: 2-Hydroxyimino-6-methyl-1-indanone
  Step B: 2-Amino-6-methyl-1-indanol (cis/trans mixture)
  Step C: (cis)-2-{[1-(2,3-Dihydro-1,4-benzodioxin-5-yl)-4-piperidyl]amino}-6-methyl-1-indanol
  Melting point: 169–170° C. (M.K.)

EXAMPLE 17
(trans)-2-{[1-(2,3-Dihydro-1,4-benzodioxin-5-yl)-4-piperidyl]amino}-6-methyl-1-indanol The procedure is as in Example 2, starting from the insoluble material obtained in Step C of Example 16.

Melting point: 203–205° C. (M.K.)

PHARMACOLOGICAL STUDY OF COMPOUNDS OF THE INVENTION

EXAMPLE 18

Binding studies

5-$HT_{1B}$ binding a) Preparation of the membranes

After dissection of guinea-pig brains, the extracted striata are frozen and then homogenised in 20 volumes (weight/volume) of 50 mM tris-HCl (pH 7.7 at ambient temperature) containing 4 mM $CaCl_2$ and 0.1% ascorbic acid, and finally centrifuged at 48,000 g for 25 minutes at 4° C. The supernatant is separated off and the precipitate is resuspended in the same volume of buffer before being incubated at 37° C. for 15 minutes in order to extract the endogenous serotonin. Finally, the suspension is centrifuged at 48,000 g for 25 minutes at 4° C. and the precipitate is resuspended in 80 volumes of buffer that contains 10 µM pargyline.

b) Binding study

The binding studies ([$^3$H]-GR 125743) are carried out in triplicate in the following buffer: 50 mM tris-HCl (pH 7.7 at ambient temperature) containing 4 mM $CaCl_2$, 0.1% ascorbic acid and 10 µM pargyline. The final volume of 500 µl is formed by 100 µl of radioligand, 100 µl of buffer or compound to be tested and 300 µl of membranes. The serotonin (10 µM) is used to define the non-specific binding. In the competition experiments, the concentration of ([$^3$H]-GR 125743) is 1 nM. The incubations are started by the addition of the membrane preparation and continue for 60 minutes at ambient temperature. The reaction is stopped by rapid filtration through filters pretreated with 0.1% polyethyleneimine, followed by three rinses with cold buffer. The specific binding represents approximately 90% of the total binding at concentrations of radioligand approaching the Kd value.

Analysis of the data

The data are analysed by non-linear regression in order to determine the Kd values (dissociation constant of the radioligand), the Bmax values (maximum number of sites) for the saturation experiments and the $IC_{50}$ values (50% inhibiting concentration) and the Hill number for the competition experiments. The inhibition constant ($K_i$) is calculated according to the Cheng-Prussof equation ($K_i=IC_{50}/1+L'/K_d$) wherein L represents the concentration of the radioligand. The results are expressed as $pK_i=-\log Ki$.

The compounds of the present invention demonstrate a very good affinity for the 5-$HT_{1B}$ receptor. Their $pK_i$ is greater than 7.4.

5-$HT_{1A}$ binding

The 5-$HT_{1A}$ receptor binding studies were carried out according to methods known and described in the literature (J. Neurochem., 1986, 47, 529–40; J. Pharmacol. Exp. Ther., 1994, 268, 337–52). The results are also expressed as $pK_i$.

The compounds of the present invention have low affinity for the 5-$HT_{1A}$ receptor. Their $pK_i$ is in the region of 6.

The two binding studies demonstrate the selectivity of the products of the invention for 5-$HT_{1B}$ receptors compared with 5-$HT_{1A}$ receptors.

EXAMPLE 19

Pharmaceutical composition: tablets

Formulation for the preparation of 1000 tablets each containing 5 mg of active ingredient Compound of Example 1 5 g
Hydroxypropyl cellulose 2 g
Wheat starch 10 g
Lactose 100 g
Magnesium stearate 2 g
Talc 2 g

What is claimed is:

1. A compound selected from those of formula (I):

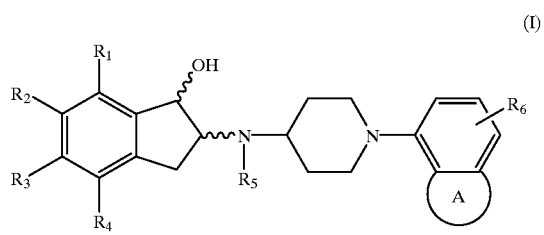

wherein:

$R_1$, $R_2$, $R_3$ and $R_4$, which may be identical or different, each represents independently of the others, hydrogen, halogen, linear or branched ($C_1$–$C_6$)alkyl, linear or branched ($C_2$–$C_6$)alkenyl, linear or branched ($C_2$–$C_6$) alkynyl, hydroxy, linear or branched ($C_1$–$C_6$)alkoxy, linear or branched ($C_1$–$C_6$)trihaloalkyl, or any one or more pairs of $R_1$, $R_2$, $R_3$, and $R_4$ in adjacent positions may form, together with the carbons of the phenyl to which they are bonded, a heterocycle, $R_5$ represents hydrogen, linear or branched ($C_1$–$C_6$)alkyl, or aryl-($C_1$–$C_6$)alkyl in which the alkyl moiety is linear or branched, $R_6$ represents hydrogen, halogen, linear or branched ($C_1$–$C_6$)alkyl, hydroxy, linear or branched ($C_1$–$C_6$) alkoxy, or linear or branched ($C_1$–$C_6$)trihaloalkyl, and A, together with the carbon atoms of the phenyl to which it is bonded, represents a heterocycle, their isomers and pharmaceutically-acceptable acid or base addition salts thereof.

2. A compound of claim 1, wherein A, together with the carbon atoms of the phenyl to which it is bonded, represents a 6-membered heterocycle containing at least one oxygen.

3. A compound of claim 1, wherein A, together with the carbon atoms of the phenyl to which it is bonded, represents chroman or 2,3-dihydro-1,4-benzodioxin.

4. A compound of claim 1, wherein $R_5$ represents hydrogen.

5. A compound of claim 1, wherein $R_1$, $R_2$, $R_3$ and $R_4$, which may be identical or different, each represents independently of the others hydrogen, halogen, linear or branched ($C_1$–$C_6$)alkyl, or any one or more pairs of $R_1$, $R_2$, $R_3$, and $R_4$ in adjacent positions may form, together with the carbons of the phenyl to which they are bonded, a 5-membered heterocycle containing one or two oxygen.

6. A compound of claim 1, wherein $R_6$ represents hydrogen or halogen.

7. A compound of claim 1 which is selected from (cis)-2-{[1-(3,4-dihydro-2H-chromen-8-yl)-4-piperidyl]amino}-5-fluoro-1-indanol and (trans)-2-{[1-(3,4-dihydro-2H-chromen-8-yl)-4-piperidyl]amino}-5-fluoro-1-indanol, and pharmaceutically-acceptable acid or base addition salts thereof.

8. A compound of claim 1 which is selected from (cis)-2-{[1-(2,3-dihydro-1,4-benzodioxin-5-yl)-4-piperidyl]amino}-1-indanol and (trans)-2-{[1-(2,3-dihydro-1,4-benzodioxin-5-yl)-4-piperidyl]amino}-1-indanol, and pharmaceutically-acceptable acid or base addition salts thereof.

9. A compound of claim 1 which is selected from (cis)-2-{[1-(3,4-dihydro-2H-chromen-8-yl)-4-piperidyl]amino}-

6-fluoro-1-indanol and (trans)-2-{[1-(3,4-dihydro-2H-chromen-8-yl)-4-piperidyl]amino}-6-fluoro-1-indanol, and pharmaceutically-acceptable acid or base addition salts thereof.

10. A compound of claim 1 which is selected from (cis)-2-{[1-(2,3-dihydro-1,4-benzodioxin-5-yl)-4-piperidyl]amino}-6-methyl-1-indanol and (trans)-2-{[1-(2,3-dihydro-1,4-benzodioxin-5-yl)-4-piperidyl]amino}-6-methyl-1-indanol, and pharmaceutically-acceptable acid or base addition salts thereof.

11. A compound of claim 1 which is selected from (cis)-2-{[1-(3,4-dihydro-2H-chromen-8-yl)-4-piperidyl]amino}-5,6-methylenedioxy-1-indanol and (trans)-2-{[1-(3,4-dihydro-2H-chromen-8-yl)-4-piperidyl]amino}-5,6-methylenedioxy-1-indanol, and pharmaceutically-acceptable acid or base addition salts thereof.

12. A compound of claim 1 which is selected from (cis)-2-{[1-(3,4-dihydro-2H-chromen-8-yl)-4-piperidyl]amino}-5,6-dihydrofuro[2,3-b]indan-1-ol and (trans)-(2-{[1-(3,4-dihydro-2H-chromen-8-yl)-4-piperidyl]amino}-5,6-dihydrofuro[2,3-b]indan-1-ol, and pharmaceutically-acceptable acid or base addition salts thereof.

13. A pharmaceutical composition comprising as active principle a therapeutically effective amount of a compound as claimed in claim 1, in combination with one or more pharmaceutically-acceptable excipients or vehicles.

14. A method of selective binding of $5HT_{1B}$ receptor in a living body comprising administering a therapeutically effective amount of a compound of claim 1 to agonistically activate the post-synaptical $5HT_{1B}$ neuronal receptor in cerebral region, peripheral sympathetic nerve endings, cerebral blood vessels, and the trigeminal primary afferent nerves.

15. The method of claim 14 wherein the agonistic activation is the treatment of pain, migraine or headache.

16. A method of selective binding of $5HT_{1B}$ receptor in a living body comprising administering a therapeutically effective amount of a compound of claim 1 to antagonistically inhibit peripheral $5HT_{1B}$ receptor.

17. The method of claim 16 wherein the antagonistic inhibition is the treatment of unstable angina or cerebral vascular accident.

18. A method of selective binding of $5HT_{1B}$ receptor in a living body comprising administering a therapeutically effective amount of a compound of claim 1 to autoregulate the dysfunctioning of serotoninergic transmission in the frontal cortex region.

19. The method of claim 18 wherein the autoregulation is the treatment of depression, anxiety, impulsive disorders, Parkinson's disease, Alzheimer's disease, bulimia, or anorexia.

* * * * *

UNITED STATES PATENT AND TRADEMARK OFFICE
CERTIFICATE OF CORRECTION

PATENT NO. : 6,153,625
DATED : November 28, 2000
INVENTOR(S) : J.L. Peglion, B. Goument, M. Millan, A. Newman-Tancredi It is certified that error appears in the above-identified patent and that said Letters Patent is hereby corrected as shown below:

Column 5, line 66: "$R_5$," should read: -- $R_{,5}$, --.
    Page 7, line 11

Column 7, line 32: "1-7-Chloro-2,3-dihydro[1,4]" should read -- 1-(7-Chloro-2,3-dihydro[1,4] --.
    Page 10, line 17

Column 9, line 64: "-11-indanol" should read:
-- -1-indanol --. Page 14, line 22

Column 10, line 22(approx): "piperidyllamino]-6," should read: -- piperidyl]amino}-6,".
    Page 15, line 18

Column 10, line 51(approx): "1,4-bezodioxin-5-yl_" should read: -- 1,4-bezodioxin-5-yl) --.
    Page 17, line 1

Signed and Sealed this

Eighth Day of May, 2001

Attest:

NICHOLAS P. GODICI

*Attesting Officer*     Acting Director of the United States Patent and Trademark Office